United States Patent
Shimizu et al.

(10) Patent No.: US 10,413,680 B2
(45) Date of Patent: Sep. 17, 2019

(54) INJECTION NEEDLE ASSEMBLY AND INJECTOR PROVIDED THEREWITH FOR INJECTING DRUG SOLUTION INTO UPPER LAYER OF SKIN

(71) Applicant: TERUMO KABUSHIKI KAISHA, Tokyo (JP)

(72) Inventors: Sakiko Shimizu, Kanagawa (JP); Sayaka Omori, Kanagawa (JP); Kazunori Koiwai, Kanagawa (JP); Yoichiro Iwase, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/654,559

(22) Filed: Jul. 19, 2017

(65) Prior Publication Data

US 2017/0312453 A1 Nov. 2, 2017

Related U.S. Application Data (63) Continuation of application No. PCT/JP2015/075499, filed on Sep. 8, 2015.

(30) Foreign Application Priority Data

Jan. 20, 2015 (JP) .................................. 2015-008648

(51) Int. Cl.
*A61M 5/32* (2006.01)
*A61M 5/158* (2006.01)
(Continued)

(52) U.S. Cl.
CPC ......... *A61M 5/3286* (2013.01); *A61B 17/205* (2013.01); *A61M 5/158* (2013.01);
(Continued)

(58) Field of Classification Search
CPC ........ A61M 5/32; A61M 5/3286; A61M 5/28; A61M 5/30; A61M 5/31; A61M 5/37; A61M 5/42; A61M 5/46; A61M 5/162
(Continued)

(56) References Cited

U.S. PATENT DOCUMENTS 3,308,822 A * 3/1967 De Luca ............. A61M 5/3286
604/274
5,328,483 A * 7/1994 Jacoby .................. A61M 5/282
222/213

(Continued)

FOREIGN PATENT DOCUMENTS

EP 2545949 A1 1/2013
EP 2554202 A1 2/2013
(Continued)

OTHER PUBLICATIONS

Syringe Needle Gauge Chart. Datasheet [online]. Sigma-Aldrich Corporation, 2014 [retrieved on Aug. 20, 2018]. Retrieved from Internet: <https://www.sigmaaldrich.com/chemistry/stockroom-reagents/learning-center/technical-library/needle-gauge-chart.html>.*

(Continued)

*Primary Examiner* — Nathan R Price
*Assistant Examiner* — Nidah M Hussain
(74) *Attorney, Agent, or Firm* — Foley & Lardner LLP (57) ABSTRACT

A needle assembly includes: a needle comprising a hollow needle tube, a needle tip at a distal end of the hollow needle tube, and a cutting face disposed adjacent to the needle tip; and a needle hub that includes a tip and a base end, and holds the needle at the needle tip. The needle hub includes a needle tip side end face from which the needle tip projects. An outer diameter of the needle is within a range of 0.15 mm to 0.20 mm, inclusive. A projection needle length extending from (Continued)

the needle tip side end face to the needle tip is within a range of 0.50 mm to 1.25 mm, inclusive. A needle body length extending from the needle tip side end face to a proximal end of the cutting face in within a range of 0.10 mm to 0.70 mm, inclusive.

13 Claims, 4 Drawing Sheets

(51) Int. Cl.
    *A61M 5/28*     (2006.01)
    *A61M 5/34*     (2006.01)
    *A61M 5/46*     (2006.01)
    *A61M 5/315*    (2006.01)
    *A61B 17/20*    (2006.01)

(52) U.S. Cl.
    CPC ............... *A61M 5/28* (2013.01); *A61M 5/32* (2013.01); *A61M 5/3293* (2013.01); *A61M 5/34* (2013.01); *A61M 5/46* (2013.01); *A61M 5/31531* (2013.01); *A61M 5/329* (2013.01)

(58) Field of Classification Search
    USPC .......................................................... 604/19
    See application file for complete search history.

(56) References Cited

U.S. PATENT DOCUMENTS

| | | | | |
|---|---|---|---|---|
| 6,494,865 B1* | 12/2002 | Alchas | ............... | A61M 5/46 604/192 |
| 6,517,521 B1* | 2/2003 | Ly | ............... | A61M 5/329 604/239 |
| 6,517,523 B1* | 2/2003 | Kaneko | ............... | A61M 5/3286 163/5 |
| 8,986,280 B2* | 3/2015 | Pettis | ............... | A61M 5/158 604/117 |
| 9,017,299 B2* | 4/2015 | Iwase | ............... | A61M 5/158 264/678 |
| D787,667 S * | 5/2017 | Iwase | ............... | D24/130 |
| 9,757,526 B2* | 9/2017 | Iwase | ............... | A61M 5/178 |
| 9,913,948 B2* | 3/2018 | Iwase | ............... | A61M 5/3287 |
| 2002/0038111 A1* | 3/2002 | Alchas | ............... | A61M 5/46 604/500 |
| 2002/0045858 A1* | 4/2002 | Alchas | ............... | A61M 5/3129 604/117 |
| 2002/0193778 A1* | 12/2002 | Alchas | ............... | A61M 5/158 604/506 |
| 2005/0027239 A1* | 2/2005 | Stout | ............... | A61M 5/30 604/68 |
| 2005/0033230 A1* | 2/2005 | Alchas | ............... | A61M 5/326 604/117 |
| 2007/0185460 A1* | 8/2007 | Vedrine | ............... | A61M 5/343 604/240 |
| 2009/0023127 A1* | 1/2009 | Yu | ............... | A01N 1/02 435/1.2 |
| 2009/0137949 A1* | 5/2009 | Landau | ............... | A61M 5/30 604/70 |
| 2010/0137831 A1* | 6/2010 | Tsals | ............... | A61M 5/3243 604/506 |
| 2011/0077602 A1* | 3/2011 | Yokota | ............... | A61M 5/32 604/239 |
| 2011/0245776 A1* | 10/2011 | Kendall | ............... | A61B 17/205 604/173 |
| 2011/0275994 A1* | 11/2011 | Iwase | ............... | A61M 5/425 604/117 |
| 2013/0079729 A1* | 3/2013 | Yokota | ............... | A61M 5/3129 604/222 |
| 2013/0096502 A1 | 4/2013 | Kawamoto et al. | | |
| 2013/0218102 A1 | 8/2013 | Iwase et al. | | |
| 2014/0052099 A1* | 2/2014 | Iwase | ............... | A61M 5/3287 604/506 |
| 2014/0363492 A1* | 12/2014 | Prestrelski | ............... | A61K 9/0014 424/450 |
| 2014/0364805 A1* | 12/2014 | Llewellyn-Hyde | ............... | A61M 5/2033 604/111 |
| 2015/0018798 A1* | 1/2015 | Tornsten | ............... | A61M 5/3286 604/506 |
| 2016/0303332 A1* | 10/2016 | Iwase | ............... | A61M 5/3286 |
| 2016/0317761 A1* | 11/2016 | Iwase | ............... | A61B 17/20 |
| 2016/0339185 A1* | 11/2016 | Tornsten | ............... | A61M 5/32 |
| 2017/0056586 A1* | 3/2017 | Merchant | ............... | A61M 5/1626 |
| 2017/0086725 A1* | 3/2017 | Woo | ............... | A61B 5/150106 |
| 2018/0015234 A1* | 1/2018 | Iwase | ............... | A61M 5/3129 |
| 2018/0146983 A1* | 5/2018 | Ueda | ............... | A61M 5/158 |
| 2018/0193572 A1* | 7/2018 | Koska | ............... | A61M 5/282 |
| 2018/0199982 A1* | 7/2018 | Hoey | ............... | A61B 18/04 |
| 2018/0214639 A1* | 8/2018 | Takemoto | ............... | A61M 5/3213 |

FOREIGN PATENT DOCUMENTS

| | | |
|---|---|---|
| JP | 2006-280503 A | 10/2006 |
| JP | 2011-206273 A | 10/2011 |
| JP | 2011-212185 A | 10/2011 |
| JP | 2012-115336 A | 6/2012 |
| WO | WO 2004004803 A2 * 1/2004 ......... A61M 5/2033 |
| WO | WO-2010-087524 A2 | 8/2010 |
| WO | WO-2012-153563 A1 | 11/2012 |
| WO | WO-2012-157318 A1 | 11/2012 |

OTHER PUBLICATIONS

International Search Report issued in corresponding application No. PCT/JP2015/075499 dated Dec. 15, 2015.
Extended European Search Report dated Sep. 4, 2018 in corresponding application No. 15878853.9.

* cited by examiner

INJECTION NEEDLE ASSEMBLY AND INJECTOR PROVIDED THEREWITH FOR INJECTING DRUG SOLUTION INTO UPPER LAYER OF SKIN

CROSS-REFERENCE TO RELATED APPLICATION

This application is a bypass continuation of PCT Application No. PCT/JP2015/075499, filed on Sep. 8, 2015, which claims priority to Japanese Application No. 2015-008648, filed on Jan. 20, 2015. The contents of both of these application are hereby incorporated by reference in their entireties.

BACKGROUND

The present disclosure relates to a needle assembly for injecting a small amount of a chemical, such as vaccine, into a skin upper layer near a skin surface, particularly into a target portion in a dermal layer near an epidermal layer, and a syringe including this needle assembly for injection of a chemical into the skin upper layer.

A chemical such as influenza vaccine or other biologicals is generally injected into subcutaneous tissue of skin, or injected into muscle tissue located at a region deeper than subcutaneous tissue for intramuscular injection. It has become known in recent years that a dose of vaccine decreases when vaccine is injected into a target portion of a skin upper layer containing a large number of immunocompetent cells, such as the epidermis and dermis.

Skin is constituted by an epidermal layer located at the surface of the skin and having a thickness ranging from 50 μm to 200 μm, a dermal layer continuing from the epidermal layer and having a thickness ranging from 0.5 mm to 3.5 mm, and a subcutaneous tissue layer located at a portion deeper than the dermal layer. Immunocompetent cells such as Langerhans' cells present in stratum spinosum epidermidis within the epidermal layer and a large number of dendritic cells within dermis present in the dermal layer near the epidermal layer are dendritic, and have receptors having a skin immunity function to react to outside antigens.

The epidermal layer is an extremely thin layer located on the surface of skin and having a thickness ranging from only 50 μm to 200 μm from the skin surface. In addition, the epidermal condition and thickness considerably differ depending on ages such as adults, juveniles, children, and infants, and further on genders, individuals, and disease and treatment histories. Accordingly, it is extremely difficult to inject an extremely small amount of vaccine, i.e., an amount of 200 μL or smaller, selectively into stratum spinosum epidermidis containing Langerhans' cells of these persons subjected to vaccine injection by using a needle that is considerably larger than the layer thickness of the epidermal layer for reasons of strength and manufacture of the needle.

It is expected that immunocompetence can be improved and a vaccine dose can be reduced if the vaccine is injected selectively into a skin upper layer corresponding to an epidermal layer and a dermal layer and located near the stratum spinosum epidermidis containing Langerhans' cells or the dermal layer containing dendritic cells within the dermis.

The skin upper layer contains a large volume of elastic fibrous tissue such as elastin and collagen, and therefore is harder than subcutaneous tissue. In this case, pain may be generated by injection of a large amount of a chemical into the skin upper layer. Accordingly, it is necessary to reduce the amount of the chemical injected into the skin upper layer to an extremely small amount, such as 200 μL or smaller, preferably 100 μL or smaller.

For meeting this necessity, there has been investigated development of an efficient syringe capable of diffusing an extremely small amount of a chemical toward Langerhans' cells, and further injecting a vaccine selectively into a dermal layer located near epidermis and containing a large number of dendritic cells within the dermis to form a wheal at which the vaccine is to be maintained for a period of time.

For example, there is known a syringe constituted by a cylinder body for storing a chemical, and a needle assembly including a needle, and developed for injecting a small amount of a chemical into any part of a dermal layer of a skin upper layer. The needle assembly is separated from the cylinder body, and attached to a chemical discharge tube located at a tip of the cylinder body immediately before injection.

For example, JP 2011-212185 A discloses a chemical injection device including: a cylinder body which includes a liquid chamber storing a chemical; a pusher which is constituted by a gasket attached to a plunger and shifting inside the cylinder body; a cylindrical holding portion provided along a cylinder body outer circumference; a connection portion which connects the cylinder body and an end of the holding portion; and a needle assembly that includes a needle hub for holding a needle and injects a chemical from a needle tip slightly projected from the needle hub into a skin upper layer. A chemical discharge tube disposed at a cylinder body tip is pressed into a fitting hole of the needle assembly to be attached to the needle assembly.

SUMMARY

An epidermal layer is thin and considerably different depending on ages, genders, individuals, and disease and treatment histories. In this case, a depth of an injection portion in a dermal layer near epidermis is difficult to unambiguously determine. Accordingly, a projection length of the needle tip slightly projecting from the needle hub is difficult to unambiguously determine. When the length of the needle inserted into skin is extremely small, vaccine more easily leaks from epidermis and does not produce sufficient immunocompetence. When the needle length is extremely large, vaccine is injected into a deep portion or subcutaneous tissue of the dermal layer containing a smaller number of dendritic cells within the dermis. In this case, the vaccine is difficult to diffuse toward Langerhans' cells and dendritic cells within the dermis, and therefore does not produce sufficient immunocompetence.

Accordingly, even when the length of the needle inserted into skin is controlled, it is still difficult to widely inject a desired amount of vaccine into an injection portion within a dermal layer near epidermis to form a wheal without leakage from the skin surface to the outside of the body regardless of ages, genders, individuals, and medical treatment histories. It is especially difficult to inject an extremely small amount of vaccine selectively into the stratum spinosum epidermidis of a person subjected to vaccine injection and having particularly thin skin, such as infants and steroid-dosed patients having thin skin as a result of a side effect of long-term injection of steroid, among general persons subjected to vaccine injection.

Certain embodiments described in this disclosure have been developed to solve the aforementioned problems. It is an object of the present disclosure to provide a needle assembly, and a chemical injection syringe including the needle assembly for injection into a skin upper layer, the needle assembly and the syringe being capable of injecting a chemical, such as a vaccine, selectively into a skin upper layer, particularly into a relatively shallow portion in a dermal layer near an epidermal layer of general persons subjected to chemical injection. Further, it is an object of the present disclosure to allow for such capability in persons having a normal dermal thickness, infants having thinner dermis than that of adults, and steroid-dosed patients, regardless of ages, genders, individuals, and medical treatment histories, to form a wheal without leakage of the chemical from the skin surface, and produce or develop sufficient medical effects such as immunocompetence even with an extremely small amount of the chemical.

A needle assembly according to one embodiment includes: a needle including a needle tube that includes a needle hole communicated from a needle tip to a needle base end, and a cutting face disposed at the needle tip; and a needle hub that includes a tip and a base end, and holds the needle at the tip. The needle hub includes a needle tip side end face from which the needle tip projects. The needle is configured such that an outer diameter is in a range from 0.15 mm (inclusive) to a length smaller than 0.20 mm, that a projection needle length extending from the needle tip side end face to the needle tip ranges from 0.50 mm (inclusive) to 1.25 mm (inclusive), and that a needle body length extending from the needle tip side end face to the cutting face ranges from 0.10 mm (inclusive) to 0.70 mm (inclusive).

In one aspect, the needle is configured such that a cutting face length of the cutting face ranges from 0.30 mm (inclusive) to 0.75 mm (inclusive).

In one aspect, a wall thickness of the needle tube ranges from 0.02 mm (inclusive) to 0.05 mm (inclusive).

In one aspect, the cutting face may include a first cutting face portion near the needle base end, and a second cutting face portion and a third cutting face portion that form a ridgeline at the needle tip on a boundary between the second cutting face portion and the third cutting face portion. Note that the "base end" refers to the side opposite to the needle tip.

In one aspect, a first cutting face portion cutting angle formed by a center axial line of the needle tube and the first cutting face portion is more acute than a ridgeline cutting angle formed by the center axial line and the ridgeline.

In one aspect, the first cutting face portion cutting angle is more acute than each of a second cutting face portion cutting angle and a third cutting face portion cutting angle formed by the center axial line and the second cutting face portion and the third cutting face portion, respectively.

In one aspect, the first cutting face portion cutting angle ranges from 10° (inclusive) to 35° (inclusive), that the ridgeline cutting angle ranges from 15° (inclusive) to 40° (inclusive), and that each of the second cutting face portion cutting angle and the third cutting face portion cutting angle ranges from 20° (inclusive) to 55° (inclusive).

In one aspect, lubricant containing silicone resin may be applied to the surface of the needle.

In one aspect, the needle hub maybe provided coaxially with the needle, and include an adjustment portion that allows projection of the needle tip and the cutting face and adjusts the projection needle length. In this case, the needle tip side end face is provided at a tip of the adjustment portion.

In one aspect, the needle hub may be provided coaxially with the adjustment portion, and include a cylindrical stabilization portion that surrounds the adjustment portion and is disposed away from the adjustment portion.

In another embodiment, a chemical injection syringe for injection of a chemical into a skin upper layer includes the needle assembly described above.

According to one aspect of the chemical injection syringe, the skin upper layer is a dermal layer of a human, and the projection needle length and the cutting face length are configured such that the opening of the needle hole near the needle tip reaches a target portion for injection in the dermal layer near epidermis.

According to one aspect of the chemical injection syringe, the chemical is injected into the skin upper layer that includes the dermal layer having a length of at least about 1.0 mm, for example.

According to one aspect of the chemical injection syringe, an outer cylinder is provided, the outer cylinder sealing and storing the chemical inside the outer cylinder by using a gasket inserted from a cylinder base end, and the outer cylinder including a chemical discharge tube at a cylinder tip, the chemical being discharged through the chemical discharge tube. In this case, the chemical discharge tube of the outer cylinder is connected to the base end of the needle hub.

According to one aspect of the chemical injection syringe, the chemical injection syringe may be a pre-filled syringe, and the chemical may be a biological.

According to one aspect of the chemical injection syringe, a plunger configured to be pressed with a force in a range between 3 N to 35 N, inclusive to inject the chemical into the skin upper layer is connected to the gasket.

According to one aspect of the chemical injection syringe, a fitting cylinder may have a tip and base end, and include a fitting hole that is communicated from the tip to the base end. In this case, the fitting hole is configured such that the base end of the needle hub is fitted into the tip of the fitting hole, and that the chemical discharge tube of the outer cylinder is fitted into the base end of the fitting hole.

According to one aspect the chemical injection syringe, the syringe includes an elastic body disposed near the base end of the needle hub, the needle being inserted through the elastic body.

A needle assembly according to certain embodiments of this disclosure is capable of stably and securely injecting a chemical, such as an extremely small amount of vaccine, selectively into a skin upper layer, particularly a relatively shallow target portion in a dermal layer near an epidermal layer of a general person subjected to chemical injection and having a normal skin thickness, and further of an infant and a long-term steroid-dosed patient having a smaller skin thickness than that of adults, regardless of differences in ages, genders, individuals, and medical treatments.

It is extremely difficult to inject a chemical into a skin upper layer of a person subjected to chemical injection and having thin skin, such as an infant and a steroid-dosed patient, in comparison with a person subjected to chemical injection and having a normal dermal thickness. The needle assembly according to certain embodiments of the present disclosure is capable of securely injecting a chemical into the skin upper layer without leakage from a skin surface. The needle assembly is capable of injecting a chemical into a skin upper layer, forming a wheal by the chemical arriving thereat, and allowing the chemical to be maintained for a period of time to produce or develop sufficient medical effects such as immunocompetence even by an extremely small amount of the chemical.

Accordingly, the needle assembly is capable of producing immunocompetence equivalent to that of subcutaneous injection or intramuscular injection for a person including an infant or a steroid-dosed patient having a small dermal thickness even when a dose of a chemical of a biological such as influenza vaccine is reduced to an amount ranging from ½ to ⅕ of that of subcutaneous injection or intramuscular injection. Accordingly, sufficient immunocompetence to viruses develops in bodies of any persons subjected to chemical injection for prevention of infectious diseases, regardless of the thickness of the dermal thickness. In addition, reduction of medical expenses is achievable.

The needle assembly may include a thin needle having an outside diameter ranging from 0.15 mm (inclusive) to a length smaller than 0.20 mm. Accordingly, pain is not easily felt at the time of insertion of a needle or injection of a chemical into a person subjected to chemical injection.

According to a chemical injection syringe including the needle assembly for injection of a chemical into a skin upper layer, an outer cylinder and the needle assembly are liquid-tightly connected to each other with pressure resistance of 3 MPa or higher even when a chemical discharge tube is pressed into a fitting hole with small force at the time of attachment between the needle assembly including a needle hub and the outer cylinder. Accordingly, the chemical does not leak from the chemical injection syringe.

According to the chemical injection syringe including the needle assembly for injection of a chemical into a skin upper layer, the chemical securely reaches the skin upper layer even when the chemical is pressed by a plunger with small force. Accordingly, injection failure does not occur even when the chemical is self-injected by a person subjected to chemical injection.

DETAILED DESCRIPTION

Hereinafter described in detail are a needle assembly, and a chemical injection syringe including this needle assembly for injection into a skin upper layer according to certain embodiments. The scope of the present invention is not limited to the embodiments described herein.

Figure 1:
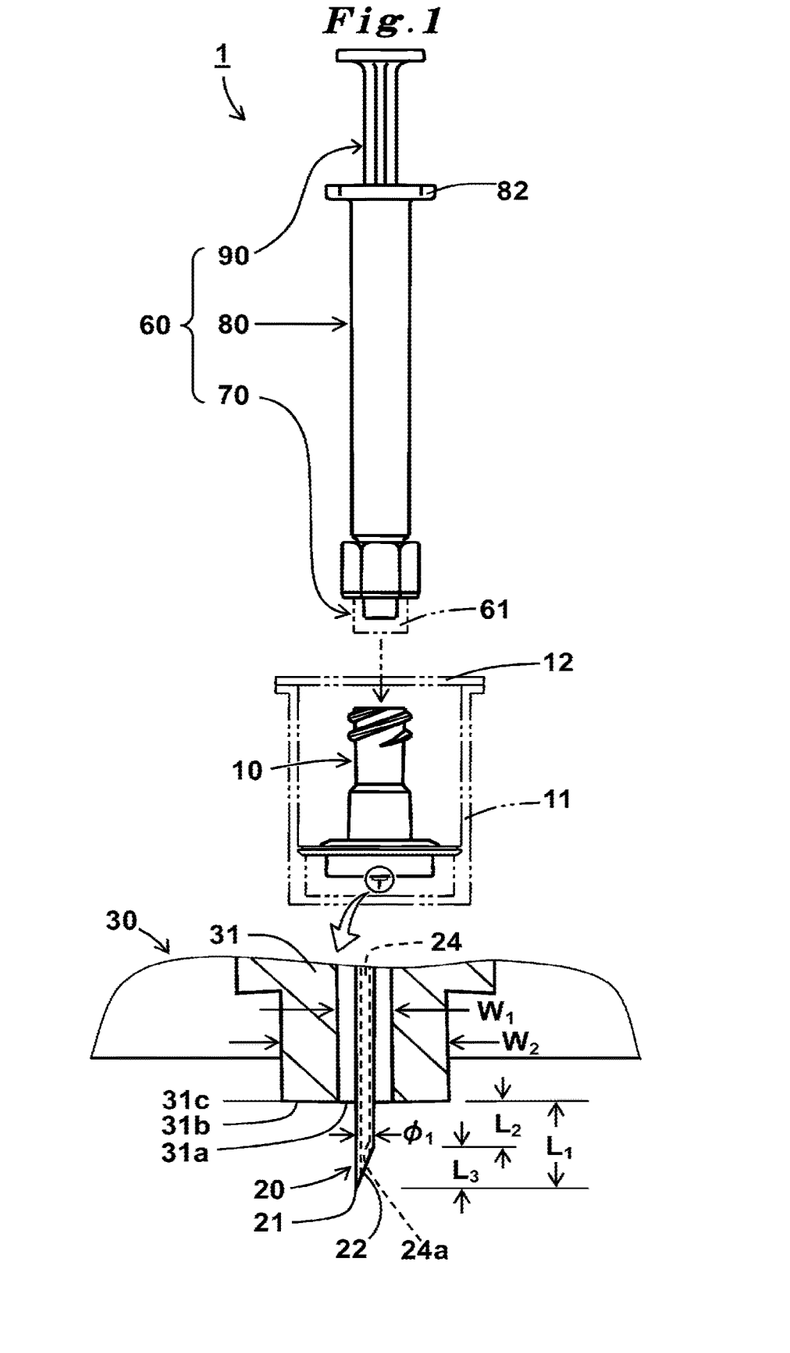
FIG. 1 is an exploded front view illustrating a needle assembly according to one embodiment, and a chemical injection syringe including this needle assembly for injection into a skin upper layer.
Figure 2A:
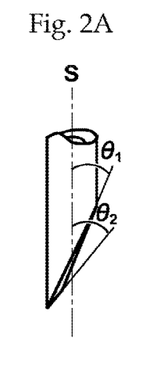
FIGS. 2A to 2E are partial enlarged views of a needle of the needle assembly according to one embodiment.
Figure 2B:
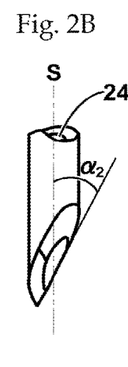
Figure 2C:
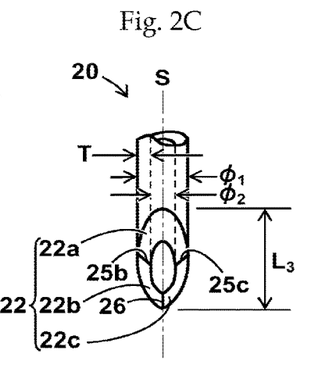
Figure 2D:
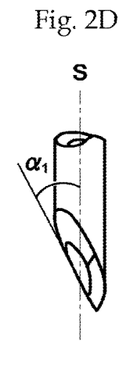
Figure 2E:
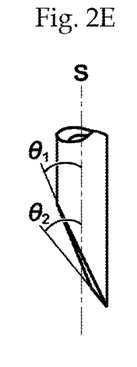

A chemical injection syringe 1 for injection into a skin upper layer, which is a syringe including the needle assembly according to one embodiment, is hereinafter described with reference to FIG. 1. FIG. 1 is an exploded front view illustrating the chemical injection syringe 1 for injection into a skin upper layer in a condition prior to use. The chemical injection syringe 1 for injection into a skin upper layer includes a syringe body 60 constituting a pre-filled syringe, and a needle assembly 10.

A needle 20 of the chemical injection syringe 1 for injection into a skin upper layer is constituted by a lancet point needle as illustrated in FIGS. 2(a) through 2(e) as viewed in various directions.

The chemical injection syringe 1 for injection into a skin upper layer is described in more detail with reference to FIG. 3 as well, i.e., a schematic partial cross-sectional view illustrating the syringe body 60 in a condition immediately before detachably attached and connected to the needle assembly 10.

The syringe body 60 includes a cylindrical outer cylinder 80, a chemical discharge tube 70 provided at a tip of the outer cylinder 80, and a pusher 90 which includes a gasket 91 inserted into the outer cylinder 80 from a cylinder base end, and a plunger 92 connected to a base end of the gasket 91. A chemical 81 is sealed between the gasket 91 and the chemical discharge tube 70. The needle assembly 10 includes the needle 20 constituted by a needle tube, a needle hub 30 holding the needle 20 via a needle holding portion 36, an elastic body 40 including an upper recess 46 penetrated by the needle 20, and a fitting cylinder 50 which accommodates the elastic body 40 and the needle holding portion 36 of the needle hub 30, and includes a fitting hole 57 having a female taper 54 and open to a base end 58.

According to the chemical injection syringe 1 for injection into a skin upper layer, a needle tip 21 is inserted into a skin upper layer of skin 100 of a person subjected to injection of the chemical 81, particularly a relatively shallow target portion 102a in a dermal layer 102 near an epidermal layer 103 to inject an extremely small amount of the chemical 81, i.e., a biological such as influenza vaccine (see FIG. 4), and form a wheal.

The needle assembly 10 is initially described.

The needle 20 penetrates the center of the needle hub 30 to be held thereat. The needle 20 projects from a needle tip side end face 31b of the needle hub 30 (see FIG. 1).

The needle 20 is constituted by a needle tube having a tube shape. The needle 20 includes the needle tip 21 projecting from the needle hub 30 of the needle assembly 10 and forming a cutting face 22 to be inserted into the skin 100, and a needle base end 23 accommodated inside the needle assembly 10 and extending substantially perpendicularly to a center axial line of the needle assembly 10. An opening 24a of a needle hole 24 formed in the needle tube opens to the cutting face 22 of the needle 20.

The needle 20 is constituted by a needle tube having an outside diameter $\varphi_1$ in a range from 0.15 mm (inclusive) to a length smaller than 0.20 mm. This size of the needle tube corresponds to an outside diameter of 34 or 35 gauge in conformity with standards of International Organization for Standardization (ISO) for medical needle tubes (ISO9626: 1991/Amd.1: 2001(E)). When the outside diameter $\varphi_1$ of the needle 20 is small, a pain is difficult to produce. However, discharge pressure of the chemical considerably increases with reduction of an inside diameter $\varphi_2$. In this case, injection of the chemical by a person injecting the chemical becomes difficult. When the inside diameter $\varphi_2$ is enlarged with the outside diameter $\varphi_1$ kept unchanged to reduce the discharge pressure of the chemical, the thickness of the wall of the needle tube (wall thickness) decreases. In this case, the needle may be difficult to insert into skin due to easy bending of the needle tube. A wall thickness T of the needle tube of the needle 20 needs to fall within a range from 0.02 mm (inclusive) to a length smaller than 0.05 mm for these reasons. When the wall thickness T is smaller than 0.02 mm, strength sufficient for insertion of the needle tube is difficult to secure. When the wall thickness T is larger than 0.05 mm, the chemical 81 is difficult to discharge by excessive reduction of the inside diameter $\varphi_2$.

As illustrated in FIGS. 1 and 2, the needle 20 is configured such that a projection needle length $L_1$ from the needle tip side end face 31b to the needle tip 21 is in a range from 0.50 mm (inclusive) to 1.25 mm (inclusive), preferably from 0.50 mm (inclusive) to a length smaller than 1.05 mm, that a needle body length $L_2$ from the needle tip side end face 31b to the cutting face 22 is in a range from 0.10 mm (inclusive) to 0.70 mm (inclusive), preferably from 0.20 mm (inclusive) to 0.45 mm (inclusive), and that an axial length of the cutting face 22 (cutting face length) $L_3$ is in a range from 0.30 mm (inclusive) to 0.75 mm (inclusive), preferably from 0.30 mm (inclusive) to 0.65 mm (inclusive). When the projection needle length $L_1$ is smaller than 0.50 mm, the needle is difficult to insert into skin. In this case, leakage of the chemical may be caused. When the projection needle length $L_1$ exceeds 1.25 mm, the chemical is difficult to inject selectively into a skin upper layer of a person subjected to injection of the chemical and having a smaller dermal thickness than an ordinary dermal thickness. In this case, the chemical may be injected into a deep portion or subcutaneous tissue of the dermal layer containing a smaller number of dendritic cells, or subcutaneous tissue. When the needle body length $L_2$ is smaller than 0.10 mm, the needle hole 24 of the inserted needle 20 is not completely inserted into skin, but protrudes from a skin surface and leaks the chemical from the skin surface. When the needle body length $L_2$ exceeds 0.70 mm, the entire projection needle length also increases. Accordingly, the chemical may be injected into a deep portion or subcutaneous tissue of the dermal layer containing a smaller number of dendritic cells, or subcutaneous tissue. When the cutting face length $L_3$ is smaller than 0.30 mm, a cutting angle of the cutting face 22 becomes an obtuse angle. In this case, insertion resistance to skin increases, wherefore insertion of the needle becomes difficult. As a result, the chemical may leak from a skin surface, or a pain at the time of insertion may be easily produced. When the cutting face length $L_3$ exceeds 0.75 mm, the cutting angle of the cutting face 22 becomes extremely acute. In this case, a cutting process may be difficult to perform, or the needle may be bended by insertion resistance at the time of insertion of the needle due to insufficient strength of the needle.

It is preferable that each of the outside diameter $\varphi_1$, the projection needle length $L_1$, the needle body length $L_2$, and the cutting face length $L_3$ of the needle 20 falls within the foregoing range, even in consideration of tolerances in manufacture, to inject the chemical into a skin upper layer with insertion resistance equivalent to or lower than that of a 33 gauge needle (outside diameter: 0.20 mm) or larger, and securely form a wheal without leakage of the chemical for general persons subjected to injection of the chemical, such as persons having an ordinary dermal thickness, and infants and steroid-dosed patients having a small dermal thickness. The outside diameter $\varphi_1$ of the needle, the projection needle length $L_1$, and the needle body length $L_2$ are particularly important factors. A needle having a small cutting face length generally has an obtuse angle of the needle tip, and produces high insertion resistance. In this case, a needle hole may be difficult to completely insert into skin due to a rise of a pain at the time of insertion of the needle into the skin, or local expansion or distortion of the skin. However, when the plurality of factors described above are limited to the foregoing ranges, insertion resistance and a pain felt by the person subjected to injection of the chemical decrease. In addition, insertion of the needle into skin with small force, stable injection of the chemical without leakage, and formation of a wheal are achievable. The outside diameter $\varphi_1$ of the needle and the cutting face length $L_3$, or a ridgeline cutting angle and a second cutting face portion cutting angle are particularly important factors for insertion resistance.

The needle 20 may be constituted by a flat bevel needle which has the cutting face 22 cut or ground into a single face. It is preferable, however, that the needle 20 is constituted by a lancet point needle which has the cutting face 22 including a substantially flat first cutting face portion 22a cut or ground on the needle base end 23 side (upper side in FIG. 3), and substantially flat second cutting face portion 22b and third cutting face portion 22c cut or ground on the needle tip 21 side (lower part in FIG. 3) at angles different from the angle of the first cutting face portion 22a as illustrated in FIGS. 2A to 2E. The needle 20 is symmetric in the left-right direction with respect to a plane perpendicular to a sheet plane of the figure containing a center axial line S of the needle tube of the needle 20 as illustrated in FIGS. 2A to 2E.

When the needle 20 is constituted by a lancet point needle including the cutting face 22 (first cutting face portion 22a and second and third cutting face portions 22b and 22c) cut or ground in multiple stages at different angles, contact between the needle tip 21 and skin at the time of insertion becomes close to linear contact rather than point contact. In this case, skin cutting becomes easier, and a pain to be produced decreases.

In addition, it is preferable that the length of the second cutting face portion in the direction of the center axial line S is set in a range from 30% (inclusive) to 60% (inclusive) of the cutting face length $L_3$. When the length of the second cutting face portion in the center axis direction is 30% of the cutting face length $L_3$ or smaller, a cutting range of target tissue decreases. In this case, the needle is difficult to insert. When the length of the second cutting face portion in the center axis direction is 60% of the cutting face length $L_3$ or larger, a sharp projection is produced inside a jaw portion and increases a pain to be felt by a patient. Accordingly, this range is inappropriate. The length of the second cutting face portion in the center axis direction is preferably in a range from 40% (inclusive) to 50% (inclusive).

As illustrated in FIGS. 2A to 2E, the needle 20 constituted by a lancet point needle has ridgelines 25b and 25c on the boundary between the first cutting face portion 22a and the second cutting face portion 22b, and between the first cutting face portion 22a and the third cutting face portion 22c, respectively. The needle 20 further has a ridgeline 26 at a cutting tip on the boundary between the second cutting face portion 22b and the third cutting face portion 22c.

A first cutting face portion cutting angle $\theta_1$ corresponding to an elevation angle formed by the center axial line S of the needle tube with respect to the first cutting face portion 22a as a reference plane is more acute than a ridgeline cutting angle $\theta_2$ formed by the center axial line S and the ridgeline 26 at the cutting tips of the second cutting face portion 22b and the third cutting face portion 22c. The first cutting face portion cutting angle $\theta_1$ is in a range from 10° (inclusive) to 35° (inclusive), more preferably from 15° (inclusive) to 30° (inclusive). The ridgeline cutting angle $\theta_2$ is in a range from 15° (inclusive) to 40° (inclusive), more preferably from 20° (inclusive) to 35° (inclusive).

The first cutting face portion cutting angle $\theta_1$ is more acute than each of a second cutting face portion cutting angle $\alpha_1$ and a third cutting face portion cutting angle $\alpha_2$ formed by the center axial line S of the needle tube and the second cutting face portion 22b, and by the center axial line S of the needle tube and the third cutting face portion 22c, respectively. The second cutting face portion cutting angle $\alpha_1$ and the third cutting face portion cutting angle $\alpha_2$ are elevation angles formed by the second cutting face portion 22b and the center axial line S of the needle tube and by the third cutting face portion 22c and the center axial line S of the needle tube, respectively. The second cutting face portion cutting angle $\alpha_1$ is in a range from 20° (inclusive) to 55° (inclusive), more preferably from 30° to 45°. The third cutting face portion cutting angle $\alpha_2$ is in a range from 20° (inclusive) to 55° (inclusive), more preferably from 30° (inclusive) to 45° (inclusive).

Note that not the entire cutting face 22, but only the area of the first cutting face portion 22a from the needle base end 23 side to substantially the center of the cutting face 22 is symmetric in the left-right direction. The area from substantially the center of the cutting face 22 to the needle tip 21 is asymmetric in the left-right direction. Accordingly, the first cutting face portion 22a, the second cutting face portion 22b, and the third cutting face portion 22c may be configured such that the ridgeline 26 at the cutting tip is located obliquely with respect to the center axial line S of the needle tube.

Figure 4:
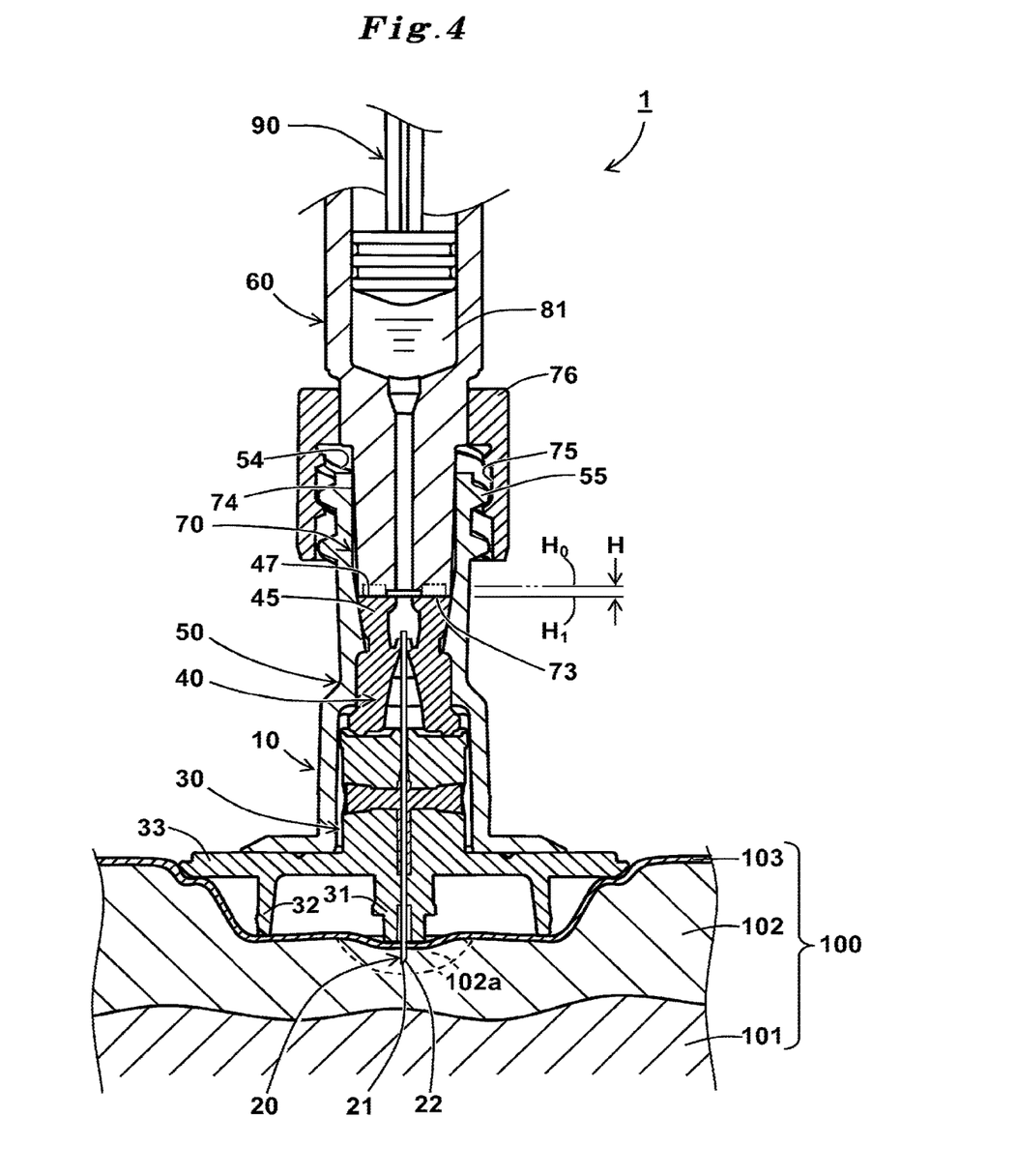
FIG. 4 is a schematic partial cross-sectional view illustrating a condition during use of the needle assembly, and the chemical injection syringe including the needle assembly for injection into a skin upper layer.

When each of the projection needle length $L_1$ of the needle hub 30 and the cutting face length $L_3$ of the cutting face 22 in the axial direction fall within the foregoing range, the needle 20 is allowed to securely inject the chemical 81, such as an extremely small amount of vaccine, selectively into the skin upper layer, particularly the relatively shallow target portion 102a in the dermal layer 102 near the epidermal layer 103 (see FIG. 4). A wheal is formed by cooperative effects of the projection needle length $L_1$ from the needle hub 30 and the cutting face length $L_3$ of the cutting face 22 in the axial direction for discharging the chemical 81 from the opening 24a of the needle hole 24 of the cutting face 22 into the target portion 102a in a state that the cutting face 22 reaches an appropriate position of the target portion 102a. When either of the length $L_1$ or $L_3$ is out of this range, there may be an increase in possibilities of leakage of the chemical from the skin 100 after injection of the chemical, no formation of a wheal, and no injection of the chemical 81, such as influenza vaccine and other biologicals, into the skin upper layer, particularly the relatively shallow target portion 102a in the dermal layer 102 near the epidermal layer 103, even in a state of arrival of the cutting face at the skin 100. In this case, the chemical 81 reduced to an amount ranging from ½ to ⅕ of that of subcutaneous injection or intramuscular injection does not produce sufficient effects such as immunocompetence.

The needle tip 21 of the needle 20 is securely inserted into the skin surface, penetrates the epidermal layer 103, and reaches the desired skin upper layer, particularly the relatively shallow target portion 102a for chemical injection in the dermal layer 102 near the epidermal layer 103. In this condition, the opening 24a of the needle hole 24 of the cutting face 22 reaches the corresponding portion.

The needle hub 30 includes the substantially cylindrical needle holding portion 36 for holding the needle 20 on the needle base end 23 side corresponding to the needle base, an adjustment portion 31 disposed at a tip 31c on the needle tip 21 side to assist injection of the chemical 81 from the needle 20, a stabilization portion 32 surrounding the adjustment portion 31, and a connection guide portion 33 supporting the adjustment portion 31 and the stabilization portion 32 and connecting to the needle holding portion 36. The respective portions 36, 31, 32, and 33 are formed integrally with each other. The needle 20 coaxially penetrates the centers of the needle holding portion 36 and the adjustment portion 31. In this case, the needle tip 21 including the cutting face 22 projects from the adjustment portion 31, while the needle holding portion 36 projects from the needle base end 23 in the opposite direction. A symmetric adhesive-filled transverse hole 35 penetrating a side wall and extending toward the center axial line S of the needle tube, and a substantially cylindrical adhesive-filled cavity 34 surrounding the needle 20 and connected to the adhesive-filled transverse hole 35 are formed approximately in the middle of the body of the substantially cylindrical needle holding portion 36. The adhesive-filled transverse hole 35 and the adhesive-filled cavity 34 are filled with an adhesive curable to fix the needle 20 in an immobile manner. The needle holding portion 36 includes a base end 38 on the needle base end 23 side. The base end 38 slightly rises in the periphery of the end face with slight radial expansion of the end outer circumference.

According to the syringe 1 including the needle 20 thus adjusted, the injected chemical 81 does not leak from the skin surface by the effects of the projection needle length $L_1$ from the needle hub 30, the cutting face length $L_3$ of the cutting face 22 in the axial direction of the needle tube, and the acute-angled cutting face 22 with respect to the center axial line S of the needle tube. In addition, even an extremely small amount of the chemical 81 forms a wheal having a diameter of several millimeters at the target portion 102a where the chemical 81 stays for a while. Accordingly, the chemical 81 is allowed to gradually diffuse toward Langerhans' cells and dendritic cells within dermis corresponding to immunocompetent cells to produce and develop sufficient medical effects such as immunocompetence. According to the chemical injection syringe 1 for injection into a skin upper layer, a sufficient amount of the chemical 81, such as influenza vaccine, reaches immunocompetent cells, and produces immunocompetence equivalent to that of subcutaneous injection or intramuscular injection even when the dose of the chemical 81 is reduced to an amount ranging from ½ to ⅕ of the amount of subcutaneous injection or intramuscular injection. Accordingly, sufficient immunity to viruses develops within the body to prevent infection regardless of individual differences in ages, such as adults, juveniles, children, and infants, and further in genders, thicknesses of epidermis and dermal layer of ordinary adjust and of infants or steroid-dosed patients.

Moreover, according to the syringe 1 including the needle 20 thus adjusted, a pain is not easily felt at the time of injection of the chemical 81 into the skin upper layer. In addition, a dead volume of the chemical 81 remaining inside the hollow part of the needle tube of the needle 20 after injection is reduced to the minimum.

The needle 20 penetrates the needle holding portion 36 and the adjustment portion 31, and is fixed by the adhesive at the adhesive-filled transverse hole 35 and the adhesive-filled cavity 34. Accordingly, the needle 20 does not rotate after injection of the chemical 81, and maintains the projection needle length $L_1$ from the needle hub 30 without change.

It is preferable that the needle 20 is made of stainless steel (SUS), for example. However, the needle 20 may be made of other materials, such as aluminum, aluminum alloy, titanium, titanium alloy, and other metals.

It is preferable that the needle 20 has the maximum insertion resistance of 0.15 N or lower in a load fluctuation curve at the time of insertion into a silicone rubber sheet of 0.5 mm at a speed of 10 mm/min. Lubricant such as silicone oil may be applied to the outer circumference of the needle 20. For example, the silicone oil used herein is silicone oil in conformity with Japanese Industrial Standards (JIS)

T3209, more specifically, cross-linking reaction silicone oil such as condensed and cross-linking reacted silicone oil, and added and cross-linking reacted silicone oil. This type of lubricant helps easy insertion of the needle 20 into the skin 100, and reduces a pain felt by a person subjected to injection of the chemical.

The needle 20 located above the axial centers of the needle holding portion 36 and the adjustment portion 31 is inserted into the surface of the skin 100 substantially at right angles at the time of injection of the chemical 81. Accordingly, the needle 20 always penetrates the skin upper layer of a human, particularly the epidermal layer 103, regardless of individual differences in ages, genders, individuals, and disease histories, and reaches the relatively shallow target portion 102a in the dermal layer 102 near the epidermal layer 103 to inject a desired amount of the chemical 81 and securely form a wheal (see FIG. 4).

The needle holding portion 36 of the needle hub 30 is connected to the connection guide portion 33 disposed at the needle tip 21 side and extended in a disk shape. The connection guide portion 33 has a larger diameter than that of the needle holding portion 36. Both the needle holding portion 36 and the cylindrical adjustment portion 31 are coaxial. The needle 20 penetrates the needle holding portion 36 and the adjustment portion 31 toward the needle tip side end face 31b of the adjustment portion 31. The adjustment portion 31 is recessed on the needle tip 21 side to expand the epidermal layer 103 and help insertion of the chemical 81 from the needle 20. The needle tip 21 of the needle 20 projects from the center of a recess 31a. The needle tip side end face 31b of the adjustment portion 31 has a sufficiently larger area than the area of a wheal formed as a blister as a result of injection of the chemical 81 into the skin upper layer. It is preferable that the needle tip side end face 31b of the adjustment portion 31 has an inside diameter $W_1$ ranging from 0.5 mm (inclusive) to 0.7 mm (inclusive), and an outside diameter $W_2$ ranging from 1.7 mm to 1.9 mm. When the needle tip side end face 31b is sized in these ranges, injection of a desired amount of the chemical 81 into the skin upper layer of a human, particularly the relatively shallow target portion 102a in the dermal layer 102 near the epidermal layer 103, prevention of leakage from the skin 100, and secure formation of a wheal are realizable regardless of individual differences.

The stabilization portion 32 has a hollow and cylindrical shape surrounding the adjustment portion 31, and has a larger diameter than each of the diameters of the adjustment portion 31 and the needle holding portion 36, and a smaller diameter than the diameter of the connection guide portion 33. The stabilization portion 32 projects from the connection guide portion 33 toward the needle tip 21. At the time of chemical injection, the needle tip 21 and the cutting face 22 of the needle 20 initially contact the skin surface, and then the needle tip side end face 31b of the adjustment portion 31 and the stabilization portion 32 contact the skin surface in this order. In this case, a clearance between the adjustment portion 31 and the stabilization portion 32 is maintained to allow expansion of the surface of the skin 100 and insertion of the needle 20 into the skin upper layer substantially at the right angles. It is preferable that the tip face of the stabilization portion 32 has an inside radius $W_3$ ranging from 5.8 mm (inclusive) to 6.2 mm (inclusive), and an outside radius $W_4$ ranging from 6.53 mm (inclusive) to 6.57 mm (inclusive). It is preferable that a width $L_5$ between the outer circumference of the adjustment portion 31 and the inner circumference of the stabilization portion 32 ranges from 4.9 mm (inclusive) to 5.3 mm (inclusive). It is preferable that the needle tip side end face 31b of the adjustment portion 31 projects from the tip face of the stabilization portion 32 by a distance $L_4$ ranging from 0.2 mm (inclusive) to 0.4 mm (inclusive). When the needle tip side end face 31b is sized in this range, the surface of the skin 100 is pulled by a press against the adjustment portion 31 and the stabilization portion 32. As a result, injection of a desired amount of the chemical 81 into the skin upper layer of a human, particularly the relatively shallow target portion 102a in the dermal layer 102 near the epidermal layer 103, and secure formation of a wheal are realizable regardless of individual differences in ages, genders, individuals, and disease histories.

It is preferable that a height $L_6$ of the stabilization portion 32 from the tip face of the stabilization portion 32 to the connection guide portion 33 is in a range from 2.9 mm (inclusive) to 3.1 mm (inclusive). It is preferable that a length (width) $W_5$ of the connection guide portion 33 from the outer surface of the stabilization portion 32 to an edge of the connection guide portion 33 is in a range from 2.9 mm (inclusive) to 3.1 mm (inclusive). In this case, a contact between the connection guide portion 33 and the surface of the skin 100 becomes an indication of arrival of the needle tip 21 of the needle 20 at the dermal layer 102.

In addition, the diameter of the connection guide portion 33 is larger than the diameter of the stabilization portion 32. Accordingly, a shift of the chemical injection syringe 1 for injection into a skin upper layer is avoidable by the contact between a sufficient area of the connection guide portion 33 and the surface of the skin 100 at the time of injection of the chemical 81.

The elastic body 40 is mounted on the needle holding portion 36 of the needle hub 30 inside a rising inner edge around the needle base end 23 side end of the needle holding portion 36. The needle 20 penetrates the axial center of the elastic body 40 on the needle base end 23 side. The elastic body 40 has a flange 41 at the needle tip 21 side end. The elastic body 40 includes a lower recess 42 recessed in a substantially cone shape and surrounding the needle 20. The elastic body 40 includes an upper recess 46 recessed in a bowl shape and surrounding the needle 20 on the needle base end 23 side. A projection portion 45 which forms a circumferential edge surrounding the upper recess 46 has a substantially flat upper end face 47. The upper end face 47 of the projection portion 45 has an area sufficient for surface contact with a tip face 73 of the chemical discharge tube 70 at a cylinder tip 73a. In addition, an opening diameter of the upper recess 46 of the elastic body 40 is equivalent to or smaller than the diameter of an opening 71 of the chemical discharge tube 70 at the tip. The upper end face 47 of the projection portion 45 comes into surface contact with the tip face 73 of the chemical discharge tube 70, and presses the chemical discharge tube 70 into the fitting hole 57 of the fitting cylinder 50 to compressively deform the projection portion 45 and liquid-tightly connect the chemical discharge tube 70 and the needle 20 (see FIG. 4). Accordingly, variations of the extremely small injection amount of the chemical 81 decrease, wherefore a desired wheal is formed with a desired amount of the chemical 81. The center of the upper recess 46 rises around the needle 20 toward the needle base end 23 side to form a valve body 44 which uniformly presses the circumference of the needle 20. The needle 20 is sandwiched between the upper recess 46 and the lower recess 42, and supported by the elastic body 40. The needle base end 23 of the needle 20 is disposed inside the upper recess 46, and slightly shifted toward the needle tip 21 from the upper end face 47 of the projection portion 45. In this case, the needle base end 23 of the needle 20 does not contact the edge of the tip face 73 of the chemical discharge tube 70. Accordingly, the projection needle length $L_1$ from the needle hub 30 is maintained without change.

The fitting cylinder 50 covers the elastic body 40 and the needle holding portion 36 of the needle hub 30 in such a manner as to surround and accommodate the elastic body 40 and the needle holding portion 36. A flange 51 provided at a lower end of the fitting cylinder 50 is bonded or welded to the connection guide portion 33 of the needle hub 30, or molded integrally with the connection guide portion 33 to be combined with the connection guide portion 33 into one body. The diameter of an approximately middle portion of the fitting cylinder 50 is reduced to a length smaller than the diameter of the lower half of the fitting cylinder 50 to form a step 52. The fitting cylinder 50 accommodates the needle holding portion 36 of the needle hub 30 in the lower half of the fitting cylinder 50. A slightly larger diameter portion 37 of the needle holding portion 36 of the needle hub 30 on the outer circumferential end on the needle base end 23 side contacts an inner wall of the fitting cylinder 50 in the lower half thereof to prevent looseness of the needle hub 30. The fitting cylinder 50 surrounds or presses the flange 41 of the elastic body 40 by the step 52.

The insertion cylinder 50 includes the fitting hole 57. The fitting hole 57 includes the female taper 54 on the needle tip 21 side. The taper ratio of the female taper 54 is set to 15/100 according to a fraction expression which defines a taper ratio as A/100 when a diameter decreases by A mm per 100 mm. At this ratio, at least the edge of the tip face 73 of a male taper 74 contacts the female taper 54 for liquid-tight connection between the outer cylinder 80 and the needle assembly 10 by pressure resistance of 3 MPa or higher even when the chemical discharge tube is pressed into the fitting hole by a small force ranging from 0.05 to 0.1 N·m at the time of attachment between the needle assembly including the needle hub and the outer cylinder in the chemical injection syringe as described above.

Slight deformation of the tip 73a of the chemical discharge tube 70 made of plastic and the female taper 54 of the fitting hole 57 increases as the chemical discharge tube 70 is more firmly pushed into the fitting hole 57.

Figure 3:
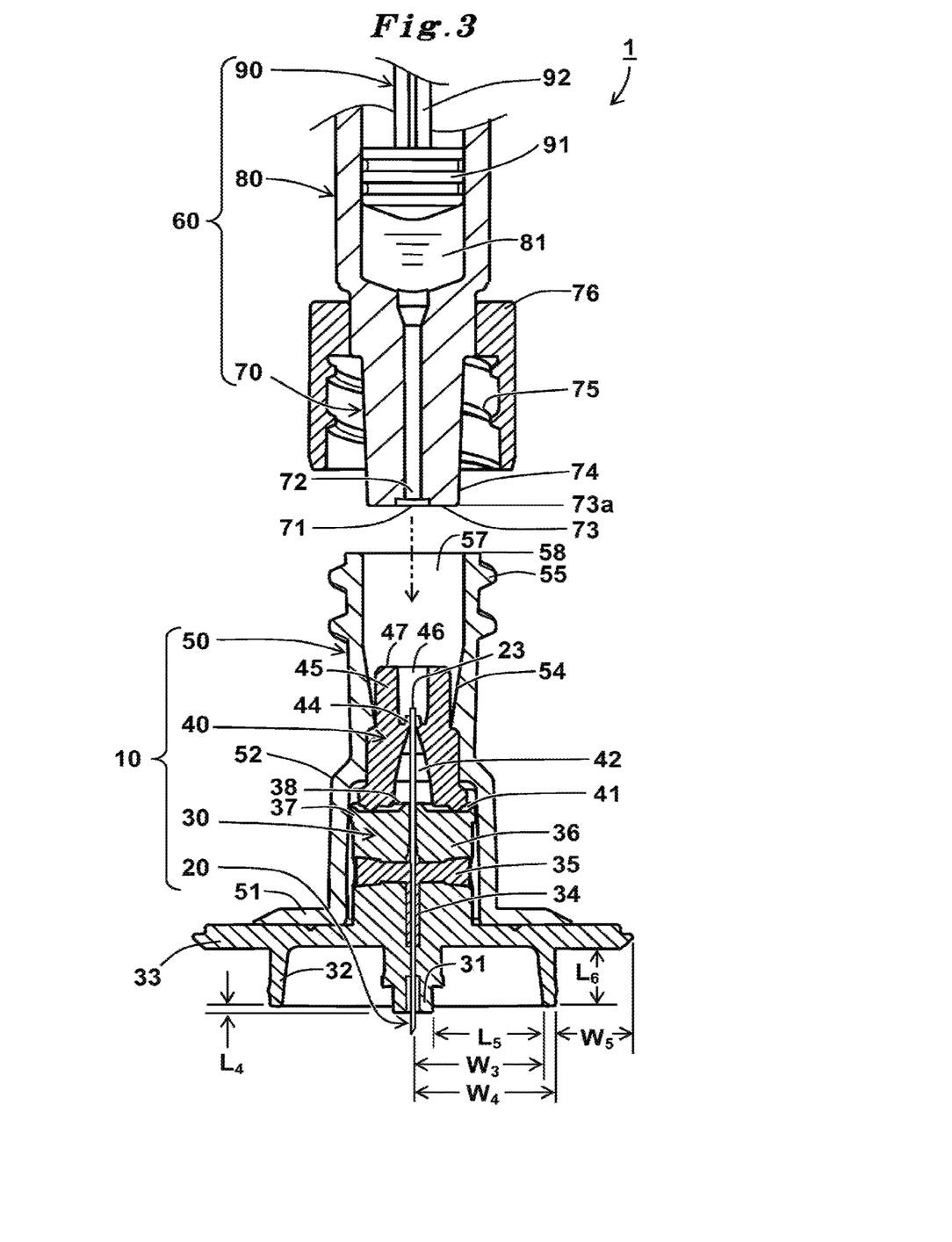
FIG. 3 is a schematic partial cross-sectional view illustrating a condition prior to use of the needle assembly, and the chemical injection syringe including the needle assembly for injection into a skin upper layer.

As illustrated in FIG. 3, the female taper 54 of the fitting cylinder 50 and the male taper 74 of the chemical discharge tube 70 are adjusted such that a fitting position $H_1$ between the female taper 54 and the male taper 74 (see FIG. 4) in the needle assembly 10 is located on the lower side, i.e., on the needle tip 21 side by a height difference H (see FIG. 4) with respect to the upper end face 47 of the projection portion 45 of the elastic body 40. Accordingly, as illustrated in FIG. 3, before attachment of the syringe body 60 to the needle assembly 10, the elastic body 40 extends the upper end face 47 of the projection portion 45 beforehand toward the opening side of the fitting hole 57 by the height difference H from the fitting position $H_1$ (see FIG. 4) between the female taper 54 and the male taper 74 to locate the upper end face 47 at an upper end face position $H_0$ in a non-fitted state (see FIG. 4). The volume, height, and shape of the projection portion 45 of the elastic body 40 inside the fitting cylinder 50 are appropriately adjusted such that the projection portion 45 is liquid-tightly expanded to the inner wall of the fitting hole 57 by compressive deformation of the upper end face 47 of the projection portion 45 in accordance with contact between the upper end face 47 and the tip face 73 of the chemical discharge tube 70 in the fitted state of the chemical discharge tube 70 into the fitting hole 57. It is further preferable that the projection portion 45 is so adjusted as to be compressively deformable to air-tightly expand toward the upper recess 46 as well as to the inner wall of the fitting hole 57 by the compressive deformation of the projection portion 45 caused by the fitting.

A male screw 55 is formed in the outer circumference of the fitting cylinder 50 to engage with a female screw 75 of a lock mechanism 76 provided on the syringe body 60.

In addition, a needle assembly cap 11 (see FIG. 1) is attached to the needle assembly 10 to cover the needle 20 including the needle tip 21 and the cutting face 22 until attachment to the syringe body 60 immediately before injection of the chemical 81.

The syringe body 60 is hereinafter described with reference to FIG. 3. The outer cylinder 80 of the syringe body 60 has a hollow cylindrical shape to store the chemical 81. The chemical discharge tube 70 is coaxially provided at the center of the outer cylinder 80 on the cylinder tip side. The gasket 91 is inserted into the outer cylinder 80 to push and discharge the chemical 81 through the chemical discharge tube 70. The chemical 81 is filled between the gasket 91 and the chemical discharge tube 70. The chemical 81 is liquid-tightly sealed by the gasket 91 to prevent leakage to the outside. The plunger 92 is connected to the base end side of the gasket 91 to constitute the pusher 90. A flange 82 provided at the base end of the outer cylinder 80 extends in two directions from the outer circumference of the outer cylinder 80 (see FIG. 1). The chemical discharge tube 70 includes a hollow hole 72 through which the chemical 81 stored in the outer cylinder 80 is discharged to the outside of the outer cylinder 80. The male taper 74 formed on the outer circumference of the chemical discharge tube 70 has an outside diameter decreasing toward the cylinder tip in conformity with ISO594-1 and ISO594-2 at a taper ratio of 6/100.

The tip face 73 which is flat and crosses the axial center direction at right angles is formed at the tip of the chemical discharge tube 70. The opening 71 of the hollow hole 72 is formed at an axial center portion of the tip face 73 as an opening through which the chemical 81 is discharged. The opening 71 has a diameter slightly larger than the diameter of the hollow hole 72. The external shape of the tip face 73 at the cylinder tip 73a of the chemical discharge tube 70, i.e., the tip outer edge of the chemical discharge tube 70 is circular. The tip face 73 of the chemical discharge tube 70 and the face of the male taper 74 of the chemical discharge tube 70 are connected to each other at the tip outer edge of the chemical discharge tube 70. The tip face 73 of the chemical discharge tube 70 has an area sufficient for securely producing compressive deformation of the elastic body 40 by contact between the tip face 73 and the elastic body 40 inside the fitting cylinder 50. The tip face 73 of the chemical discharge tube 70 comes into surface contact with the upper end face 47 of the projection portion 45 constituting the circumferential edge of the upper recess 46 of the elastic body 40 to liquid-tightly connect the chemical discharge tube 70 and the needle 20. The chemical discharge tube 70 is sealed by a chemical discharge tube cap (see FIG. 1) until a time immediately before chemical injection to prevent leakage of the chemical 81 and contamination by outside miscellaneous germs.

The chemical discharge tube 70 includes the cylindrical lock mechanism 76 disposed on the rear end side of the chemical discharge tube 70 and coaxially surrounding the chemical discharge tube 70. The cylinder of the lock mechanism 76 has a transverse cross section which has a circular inner circumference, and a hexagonal outer circumference, for example, to be picked with fingers and easily rotated. The lock mechanism 76 is constituted by a component separated from the outer cylinder 80 and the chemical discharge tube 70, and attached by bonding, engagement, screwing or the like, or molded integrally with the outer cylinder 80 and the chemical discharge tube 70, on the base end side of the chemical discharge tube 70. For fitting the chemical discharge tube 70 into the fitting hole 57 of the fitting cylinder 50, the chemical discharge tube 70 is more firmly fitted into the fitting hole 57 of the fitting cylinder 50 as the lock mechanism 76 is more deeply screwed. Accordingly, the tip face 73 of the chemical discharge tube 70 more firmly presses the projection portion 45 of the elastic body 40 as the lock mechanism 76 is more deeply screwed. However, deformations of the male taper 74 and the female taper 54 are limited even when the chemical discharge tube 70 is firmly fitted into the fitting hole 57 of the fitting cylinder 50. Accordingly, the fitting position $H_1$ (see FIG. 4) is determined in accordance with the taper ratio, the dimensional tolerance, materials of the chemical discharge tube 70 and the fitting cylinder 50, and the fastening degree of the lock mechanism 76.

The syringe body 60, the lock mechanism 76 included in the syringe body 60, the fitting cylinder 50 and the needle hub 30 of the needle assembly 10, and the plunger 92 of the pusher 90 are made of plastic such as thermoplastic resin and thermosetting resin, and/or metal. For example, plastic constituting these components is polypropylene, polycarbonate, polyethylene, or cycloolefin polymer. Metal constituting these components is stainless steel or aluminum, for example. The elastic body 40 and the gasket 91 are made of an elastic material, including: various types of rubber such as natural rubber and silicone rubber; various types of thermoplastic elastomer such as a polyurethane group and a styrene group; or a mixture of these materials.

The chemical injection syringe 1 for injection into a skin upper layer is manufactured in a following manner. The needle assembly 10 is initially manufactured in a following manner. An end of a needle tube having the outside diameter φ1 ranging from 0.15 mm (inclusive) to a length smaller than 0.20 mm is cut obliquely to the center axial line of the needle tube to form the first cutting face portion 22a. The tip side is successively cut in a direction more oblique than the cutting direction of the first cutting face portion 22a to form the second cutting face portion 22b and the third cutting face portion 22c, whereafter the needle base end side is cut into a predetermined length to produce the needle 20. The needle 20 is immersed in lubricant containing silicone resin to give lubricity to the needle 20 as necessary. Thereafter, plastic material is molded into the needle hub 30 and the fitting cylinder 50, while rubber material is molded into the elastic body 40. The needle 20 is inserted into coaxial through holes of the needle holding portion 36 and the adjustment portion 31 of the needle hub 30. An adhesive is injected through the adhesive-filled transverse hole 35 formed in the needle holding portion 36 with the needle tip 21 of the needle 20 projected from the tip 31c of the adjustment portion 31 by a desired length of insertion into the skin 100 to fix the needle holding portion 36 and the needle 20 by the adhesive. The elastic body 40 is inserted into the fitting cylinder 50 to fix the flange 41 of the elastic body 40 to the step 52 of the fitting cylinder 50. An adhesive is applied to a contact portion between the flange 51 of the fitting cylinder 50 and the connection guide portion 33 of the needle hub 30. Subsequently, the needle hub 30 including the needle 20 is inserted into the fitting cylinder 50. The needle 20 is stuck into the elastic body 40 from the needle base end 23 side, whereafter the flange 51 of the fitting cylinder 50 and the connection guide portion 33 of the needle hub 30 are bonded and fixed to each other to produce the needle assembly 10. The needle assembly 10 is covered by the needle assembly cap 11, and tightly closed by a cover 12 with thermal welding seal. The needle assembly 10 is sterilized as necessary.

On the other hand, the syringe body 60 is manufactured in a following manner. Plastic material is molded into the outer cylinder 80, the chemical discharge tube 70, and the lock mechanism 76 formed integrally with each other. Rubber material is molded into the gasket 91, while plastic material is molded into the plunger 92. Thereafter, the gasket 91 is connected to the plunger 92 to produce the pusher 90. The syringe body 60 is closed by the chemical discharge tube cap 61, whereafter the chemical 81 is filled into the outer cylinder 80 of the syringe body 60. For example, a small amount corresponding to a dead volume is added to a desired amount of the chemical 81 injected into a skin upper layer (e.g. 100 to 200 μL). The gasket 91 of the pusher 90 including the plunger 92 is inserted to produce the syringe body 60 corresponding to a pre-filled syringe. The syringe body 60 is put into a sterilized package and tightly closed. Thereafter, the syringe body 60 is sterilized as necessary.

Described hereinafter with reference to FIG. 4 is a use method for connecting the syringe body 60 to the needle assembly 10 by fitting the chemical discharge tube 70 into the fitting hole 57 of the fitting cylinder 50, and injecting the chemical 81 into a skin upper layer.

The syringe body 60 and the needle assembly 10 are unsealed (see FIG. 1). The chemical discharge tube 70 of the syringe body 60 in a state that the needle assembly cap 11 is attached to the chemical discharge tube 70 is slightly pushed into the fitting cylinder 50 of the needle assembly 10, whereafter the female screw 75 of the lock mechanism 76 surrounding the chemical discharge tube 70 is fitted into the male screw 55 of the fitting cylinder 50 of the needle assembly 10, and started to be fastened with fitting torque ranging from 0.05 to 0.4 N·m. As a result, the chemical discharge tube 70 is further inserted toward the inner side of the fitting cylinder 50.

With fastening of the lock mechanism 76, the tip face 73 of the chemical discharge tube 70 initially comes into contact with the upper end face 47 of the projection portion 45 of the elastic body 40 at the upper end face position $H_0$ in the non-fitted state. With further fastening of the lock mechanism 76, the female screw 75 and the male screw 55 are further fitted to each other, whereby the tip face 73 of the chemical discharge tube 70 starts to compressively deform the projection portion 45 of the elastic body 40 while tightly contacting the projection portion 45. With still further fastening of the lock mechanism 76, the projection portion 45 is further pressed via the upper end face 47, whereby the male taper 74 of the chemical discharge tube 70 is fitted to the female taper 54 of the fitting hole 57 of the fitting cylinder 50 and stops further fastening. As a result, the projection portion 45 of the elastic body 40 is compressively deformed up to the fitting position $H_1$ between the male taper 74 and the female taper 54.

Thereafter, the needle assembly cap 11 is removed. The needle tip 21 of the needle assembly 10 is directed toward the skin 100. The chemical injection syringe 1 for injection into a skin upper layer is pressed against the skin 100 such that the needle 20 becomes perpendicular to the skin 100. The needle tip 21 is inserted into the skin 100, while the stabilization portion 32 is pressed against the epidermal layer 103 of the skin 100. The adjustment portion 31 contacts the epidermal layer 103 of the skin 100, and pulls the surface of the epidermal layer 103 in cooperation with the stabilization portion 32 and the adjustment portion 31. The connection guide portion 33 contacts the skin 100 to stabilize the chemical injection syringe 1 without looseness. The acute cutting face 22 of the needle tip 21 of the needle 20 penetrates the epidermal layer 103. The opening 24a of the needle hole 24 of the cutting face 22 reaches the relatively shallow target portion 102a for injection in the dermal layer 102 near the epidermal layer 103, but does not reach subcutaneous tissue 101. The pusher 90 is completely pushed in this condition to inject the chemical 81. In this case, the elastic body 40 already sufficiently deformed with compression is not further compressively deformed by pressure applied to the chemical 81 from the pusher 90. The chemical 81 stays at the target 102a for injection, and does not leak toward the epidermal layer 103. Thereafter, the needle 20 is removed, and the chemical injection syringe 1 for injection into a skin upper layer is separated from the skin 100. As a result, a wheal which is several millimeters in length, has a red spot shape, and slightly expands to the outside is formed by the chemical 81 staying at the target portion 102a for injection. The chemical injection syringe 1 for injection into a skin upper layer is again closed by the needle assembly cap 11 (see FIG. 1), and discarded as medical waste.

EXAMPLES

Described hereinafter are examples of an experimentally produced chemical injection syringe for injection into a skin upper layer according to an embodiment of the present disclosure, and a chemical injection syringe according to an embodiment of the present disclosure. Injection of a chemical into a skin upper layer by using each of these syringes was evaluated. In addition, insertion resistance into silicone rubber was measured for each of the syringes.

Examples and Comparative Examples

The needle assembly 10 according to the embodiment illustrated in FIGS. 1 through 4, and the chemical injection syringe 1 for injection into a skin upper layer including the needle assembly 10 were experimentally produced. The needle 20 is constituted by a lancet point needle, corresponds to 34 gauge (outside diameter φ1: 0.18 mm), and has the projection needle length $L_1$ extending from the needle tip side end face 31b to the needle tip 21, and the cutting face length $L_3$ of the cutting face 22 in the axial direction, both the lengths determined as shown in Table 1. The first cutting face portion cutting angle θ1, the ridgeline cutting angle θ2, the second cutting face portion cutting angle α1, and the third cutting face portion cutting angle α2 are set to 27°, 32°, 37.5°, and 37.5° for example 1, 23°, 28°, 37.5°, and 37.5° for example 2, 20°, 25°, 37.5°, and 37.5° for example 3, 15°, 20°, 37.5°, and 37.5° for example 4, and 27°, 32°, 37.5°, and 37.5° for example 5, and 15°, 20°, 37.5°, and 37.5° for example 6, respectively. Chemical injection syringes shown in Table 1 were also experimentally produced as comparative examples. As shown in Table 2, the maximum insertion resistance of each needle is set to 0.15 N or lower in a load fluctuation curve at the time of insertion into a silicone rubber sheet of 0.5 mm at a speed of 10 mm/min when evaluated as an individual needle. The chemical used was medical normal saline.

The distance $L_4$ of projection of the needle tip side end face 31b of the adjustment portion 31 from the tip face of the stabilization portion 32 is 0.3 mm. The width $L_5$ between the outer circumference of the adjustment portion 31 and the inner circumference of the stabilization portion 32 is 5.1 mm. The height $L_6$ from the tip face of the stabilization portion 32 to the connection guide portion 33 is 3.0 mm. The inside radius $W_3$ of the tip face of the stabilization portion 32 is 6.0 mm. The outside radius $W_4$ of the stabilization portion 32 is 6.55 mm. The length (width) $W_5$ from the outer surface of the stabilization portion 32 to the edge of the connection guide portion 33 is 3.0 mm.

An amount of 0.1 mL of the chemical 81 was injected into a forearm flexor of each of four volunteers constituted by male and female adults by using the chemical injection syringe 1 for injection into a skin upper layer. This injection was performed by following procedures. The dermal thickness of the forearm flexor was measured by using an ultrasonic pulse-echo device, and a portion having a dermal thickness ranging from approximately 0.9 mm to 1.1 mm was selected. The range of the selected portion for injection was marked with on oil-based ink pen. The selected portion was disinfected by using ethanol for disinfection. The syringe body 60 was fitted into the needle assembly 10, whereafter the needle assembly cap 11 was removed. The chemical injection syringe 1 for injection into a skin upper layer was gripped with a press on the pusher 90 by the thumb. The chemical injection syringe 1 was perpendicularly pressed against the portion for injection selected from the skin 100 until contact between the connection guide portion 33 and the skin 100. As a result, the needle tip 21 was inserted into the skin 100. The pusher was pushed by the thumb to gradually inject the whole amount of the chemical 81 into the skin upper layer. The chemical injection syringe 1 was maintained for about two seconds after complete push of the pusher, and then separated from the skin with removal of the needle 20 out of the skin to complete injection into the skin by the chemical injection syringe 1.

(Injection Evaluation)

After injection into the skin, performed for comprehensive evaluations were visual check of the presence or absence of chemical leakage and the presence or absence of wheal formation, photographing (not shown), and measurement of the major axis of the wheal by using vernier calipers. Criteria for a success of injection into the skin was defined as no leakage of the chemical to the skin surface, and formation of a wheal. Results of the experiments are collectively shown in Table 1. Among respective numerical values in Table 1, an item of "presence or absence of chemical leakage" indicates (number of subjects having chemical leakage)/(number of subjects for injection into skin), while an item of "presence or absence of wheal formation" indicates "number of subjects having wheal formation)/(number of subjects for injection into skin).

TABLE 1

INJECTION EVALUATION RESULTS

| | NEEDLE | | | | | | | EVALUATION RESULTS | | | |
|---|---|---|---|---|---|---|---|---|---|---|---|
| | OUTSIDE DIAMETER $\phi_1$ (mm) | PROJECTION NEEDLE LENGTH $L_1$ (mm) | CUTTING FACE LENGTH $L_3$ (mm) | NEEDLE BODY LENGTH $L_{2(L1-L3)}$ (mm) | FIRST CUTTING FACE PORTION CUTTING ANGLE $\theta_1$ (°) | RIDGE-LINE CUTTING ANGLE $\theta_2$ (°) | SECOND CUTTING FACE PORTION CUTTING ANGLE $\alpha_1$ AND THIRD CUTTING FACE PORTION CUTTING ANGLE $\alpha_2$ (°) | PRESENCE/ ABSENCE OF CHEMICAL LEAKAGE | PRESENCE/ ABSENCE WHEAL | WHEAL AVERAGE MAJOR AXIS (mm) | U-TEST COMPARED WITH EXAMPLE 1 | SUCCESS/ FAILURE OF INJECTION INTO SKIN |
| EXAMPLE 1 | 0.18 (34G) | 0.50 | 0.30 | 0.20 | 27.0 | 32.0 | 37.5 | 0/5 | 5/5 | 10.3 | — | ALL SUCCESSFUL |
| EXAMPLE 2 | 0.18 (34G) | 0.50 | 0.40 | 0.10 | 23.0 | 28.0 | 37.5 | 0/5 | 5/5 | 10.3 | NO SIGNIFICANT DIFFERENCE | ALL SUCCESSFUL |
| EXAMPLE 3 | 0.18 (34G) | 0.60 | 0.50 | 0.10 | 20.0 | 25.0 | 37.5 | 0/5 | 5/5 | 9.1 | NO SIGNIFICANT DIFFERENCE | ALL SUCCESSFUL |
| EXAMPLE 4 | 0.18 (34G) | 0.70 | 0.60 | 0.10 | 15.0 | 20.0 | 37.5 | 0/5 | 5/5 | 9.7 | NO SIGNIFICANT DIFFERENCE | ALL SUCCESSFUL |
| EXAMPLE 5 | 0.18 (34G) | 1.00 | 0.30 | 0.70 | 27.0 | 32.0 | 37.5 | 0/5 | 5/5 | 8.8 | NO SIGNIFICANT DIFFERENCE | ALL SUCCESSFUL |
| EXAMPLE 6 | 0.18 (34G) | 1.00 | 0.60 | 0.40 | 15.0 | 20.0 | 37.5 | 0/4 | 4/4 | 7.6 | SIGNIFICANTLY SMALL | ALL SUCCESSFUL |
| COMPARATIVE EXAMPLE 1 | 0.20 (33G) | 1.15 | 0.60 | 0.55 | 16.0 | 21.0 | 37.5 | 0/5 | 4/5 | 4.4 | SIGNIFICANTLY SMALL | PARTIAL INJECTION INTO SKIN |
| COMPARATIVE EXAMPLE 2 | 0.18 (34G) | 0.40 | 0.30 | 0.10 | 27.0 | 32.0 | 37.5 | 3/3 | 1/3 | 0.0 | SIGNIFICANTLY SMALL | CHEMICAL LEAKAGE PRESENT |
| COMPARATIVE EXAMPLE 3 | 0.18 (34G) | 0.65 | 0.60 | 0.05 | 15.0 | 20.0 | 37.5 | 3/10 | 10/10 | 8.8 | NO SIGNIFICANT DIFFERENCE | CHEMICAL LEAKAGE PRESENT |

G IN OUTSIDE DIAMETER: GAUGE

TABLE 2

RESULTS OF INSERTION RESISTANCE TO SILICONE RUBBER

| | NEEDLE | | | | EVALUATION RESULTS | |
|---|---|---|---|---|---|---|
| | OUTSIDE DIAMETER $\varphi_1$ (mm) | FIRST CUTTING FACE LENGTH $L_3$ (mm) | FIRST CUTTING FACE PORTION CUTTING ANGLE $\theta_1$ (°) | RIDGELINE CUTTING ANGLE $\theta_2$ (°) | SECOND CUTTING FACE FIRST PORTION CUTTING ANGLE $\alpha_1$ AND THIRD CUTTING FACE PORTION CUTTING ANGLE $\alpha_2$ (°) | AVERAGE INSERTION RESISTANCE (N) | U-TEST COMPARED WITH COMPARATIVE EXAMPLE 4 |
| EXAMPLE 1 | 0.18 (34G) | 0.30 | 27.0 | 32.0 | 37.5 | 0.11 | NO SIGNIFICANT DIFFERENCE |
| EXAMPLE 2 | 0.18 (34G) | 0.40 | 23.0 | 28.0 | 37.5 | 0.10 | NO SIGNIFICANT DIFFERENCE |
| EXAMPLE 3 | 0.18 (34G) | 0.50 | 20.0 | 25.0 | 37.5 | 0.09 | SIGNIFICANTLY SMALL |
| EXAMPLE 4 | 0.18 (34G) | 0.60 | 15.0 | 20.0 | 37.5 | 0.06 | SIGNIFICANTLY SMALL |
| COMPARATIVE EXAMPLE 4 | 0.20 (33G) | 0.65 | 14.0 | 19.0 | 37.5 | 0.11 | — |

G IN OUTSIDE DIAMETER: GAUGE

According to the chemical injection syringes 1 in examples 1 through 6, which were made in accordance with embodiments of the present disclosure, the outside diameter $\varphi_1$, the projection needle length $L_1$, the needle body length $L_2$, and the cutting face length $L_3$ of the needle 20 fall within appropriate ranges. Accordingly, the chemical is injected selectively into the skin upper layer, particularly the relatively shallow target portion 102a in the dermal layer 102 near the epidermal layer 103, and a wheal is securely formed without leakage of the chemical. In addition, substantially no pain is produced during needle insertion. According to the chemical injection syringes 1 in examples 1 through 6, the needle 20 has the outside diameter $\varphi_1$ is a small size of 34 gauges, and the ridgeline cutting angle $\theta_2$ corresponding to a needle tip angle is an obtuse angle. However, insertion resistance of the chemical injection syringes 1 in the examples 1 through 6 was equivalent to insertion resistance of the chemical injection syringe including a needle which has the outside diameter $\varphi_1$ corresponding to a large size of 33 gauges, and an acute needle tip angle according to comparative example 4.

According to comparative example 1, the needle projection length of the needle 20 is larger than the length of the dermal layer. In this case, the chemical leaks into subcutaneous tissue, wherefore no wheal or only a small wheal was formed. According to comparative example 2, the needle projection length of the needle 20 was not long enough to completely enter the skin. In this case, chemical leakage toward the skin surface was caused in all of the examples, wherefore no wheal or only an extremely small wheal was formed. According to comparative example 3, the needle body length $L_2$ was not long enough to completely insert the needle hole 24 of the needle 20 into the skin. In this case, formation of a wheal was confirmed, but chemical leakage toward the skin surface was caused at considerable frequency.

It has been confirmed, based on the respective examples of the embodiment, that a chemical is successfully injected into a shallow target portion in a dermal layer near an epidermal layer without leakage of the chemical from skin when the outside diameter $\varphi_1$, the projection needle length $L_1$, the needle body length $L_2$, and the cutting face length $L_3$ of the needle 20 fall within appropriate ranges.

A chemical injection syringe for injection into a skin upper layer according to embodiments of the present disclosure is capable of securely injecting a chemical into a relatively shallow target portion in a dermal layer near an epidermal layer without leakage of the chemical from skin after chemical injection. Accordingly, the chemical injection syringe according to embodiments of the present disclosure is capable of securely and injecting a chemical, such as an extremely small amount of vaccine, selectively into a skin upper layer, particularly a relatively shallow target portion in a dermal layer near an epidermal layer regardless of individual differences in ages of adults, genders, individuals, medical treatment histories and the like.

A chemical injection syringe for injection into a skin upper layer according to embodiments of the present disclosure is applicable to injection of a small amount of chemical into a skin upper layer of a person subjected to chemical injection and having a normal skin thickness, as well as an infant and a long-term steroid-dosed patient having a small skin thickness.

REFERENCE NUMERAL LIST

1 Chemical injection syringe for injection into skin upper layer
10 Needle assembly
11 Needle assembly cap
12 Cover
20 Needle
21 Needle tip 22 Cutting face
22a First cutting face portion
22b Second cutting face portion
22c Third cutting face portion
23 Needle base end
24 Needle hole
24a Needle hole opening
25b, 25c, 26 Ridgeline
30 Needle hub
31 Adjustment portion
31a Recess
31b Needle tip side end face
31c Tip
32 Stabilization portion
33 Connection guide portion
34 Adhesive-filled cavity
35 Adhesive-filled transverse hole
36 Needle holding portion
37 Larger diameter portion
38 Base end
40 Elastic body
41 Flange
42 Lower recess
44 Valve body
45 Projection portion
46 Upper recess
47 Upper end face
50 Fitting cylinder
51 Flange
52 Step
54 Female taper
55 Male screw
57 Fitting hole
58 Base end
60 Syringe body
61 Chemical discharge tube cap
70 Chemical discharge tube
71 Opening
72 Hollow hole
73 Tip face
73a Cylinder tip
74 Male taper
75 Female screw
76 Lock mechanism
80 Outer cylinder
81 Chemical
82 Flange
90 Pusher
91 Gasket
92 Plunger
100 Skin
101 Subcutaneous tissue
102 Dermal layer
102a Target portion
103 Epidermal layer
H Height difference
H0 Upper end face position in non-fitted state
H1 Fitting position
L1 Projection needle length from needle hub
L2 Needle body length
L3 Cutting face length in axial direction
L4 Distance between end face of adjustment portion and end face of stabilization portion
L5 Width between outer circumference of adjustment portion and inner circumference of stabilization portion
L6 Height from tip face of stabilization portion to connection guide portion
W1 Inside diameter of end face of adjustment portion
W2 Outside diameter of end face of adjustment portion
W3 Inside radius of end face of stabilization portion
W4 Outside radius of end face of stabilization portion
W5 Length from outer surface of stabilization portion to edge of connection guide portion
$\varphi 1$ Outside diameter of needle
$\varphi 2$ Inside diameter of needle
$\theta 1$ First cutting face portion cutting angle
$\theta 2$ Ridgeline cutting angle
$\alpha 1$ Second cutting face portion cutting angle
$\alpha 2$ Third cutting face portion cutting angle
T Wall thickness
S Center axial line of needle tube

The invention claimed is:

1. A needle assembly comprising:
a needle comprising a hollow needle tube, a needle tip at a distal end of the hollow needle tube, and a cutting face disposed adjacent to the needle tip; and
a needle hub that includes a tip and a base end, and holds the needle at the needle tip,
wherein the cutting face includes:
a first cutting face portion at a proximal side of the cutting face, and
a second cutting face portion and a third cutting face portion that form a ridgeline at the needle tip on a boundary between the second cutting face portion and the third cutting face portion,
wherein a first cutting face portion cutting angle formed by a center axial line of the needle tube and the first cutting face portion is more acute than a ridgeline cutting angle formed by the center axial line and the ridgeline,
wherein the first cutting face portion cutting angle is more acute than each of a second cutting face portion cutting angle formed by the center axial line and the second cutting face portion, and a third cutting face portion cutting angle formed by the center axial line and the third cutting face portion,
wherein the first cutting face portion cutting angle is within a range of 10° to 35°, inclusive, the ridgeline cutting angle is within a range of 15° to 40°, inclusive, and each of the second cutting face portion cutting angle and the third cutting face portion cutting angle is within a range of 20° to 55°, inclusive,
wherein the needle hub includes a needle tip side end face from which the needle tip projects,
wherein an outer diameter of the needle is greater than or equal to 0.15 mm and less than 0.20 mm,
wherein a projection needle length extending from the needle tip side end face to the needle tip is within a range of 0.50 mm to 1.25 mm, inclusive, and
wherein a needle body length extending from the needle tip side end face to a proximal end of the cutting face is within a range of 0.10 mm to 0.70 mm, inclusive,
wherein a cutting face length of the cutting face is within a range of 0.30 mm to 0.75 mm, inclusive,
wherein a wall thickness of the needle tube is within a range of 0.02 mm to 0.05 mm, inclusive.

2. The needle assembly according to claim 1, wherein a lubricant containing silicone resin is disposed on a surface of the needle.

3. The needle assembly according to claim 1, wherein:
the needle hub is coaxial with the needle and includes an adjustment portion that allows projection of the needle tip and the cutting face and is configured to adjust the projection needle length, and the needle tip side end face is located at a tip of the adjustment portion.

4. The needle assembly according to claim 3, wherein the needle hub is coaxial with the adjustment portion and includes a cylindrical stabilization portion that surrounds the adjustment portion and is disposed away from the adjustment portion.

5. A chemical injection syringe configured for injection of a chemical into a skin upper layer, the chemical injection syringe comprising the needle assembly according to claim 1.

6. The chemical injection syringe according to claim 5, wherein:
the chemical injection syringe is configured for injection of the chemical into a dermal layer of a human, and
the projection needle length and the cutting face length are such that, upon use of the chemical injection syringe, an opening of the needle near the needle tip reaches a target portion for injection in the dermal layer near an epidermis of a human.

7. The chemical injection syringe according to claim 5, wherein:
the chemical injection syringe is configured for injection of the chemical into a dermal layer of a human, and
the chemical injection syringe is configured to inject the chemical into the skin upper layer, which includes the dermal layer that has a depth of at least 1.0 mm.

8. The chemical injection syringe according to claim 7, wherein:
the chemical injection syringe is a pre-filled syringe, and
the chemical is a biological.

9. The chemical injection syringe according to claim 5, further comprising:
an outer cylinder configured to seal and store the chemical inside the outer cylinder by using a gasket that is insertable from a cylinder base end, the outer cylinder comprising a chemical discharge tube at a cylinder tip, the chemical discharge tube being configured to discharge the chemical,
wherein the chemical discharge tube of the outer cylinder is connected to the base end of the needle hub.

10. The chemical injection syringe according to claim 9, further comprising a plunger connected to the gasket, the plunger being configured to be pressed with a force within a range of 3 N to 35 N, inclusive, to inject the chemical into the skin upper layer.

11. The chemical injection syringe according to claim 9, further comprising:
a fitting cylinder having a fitting cylinder tip and a fitting cylinder base end, and including a fitting hole that extends from the fitting cylinder tip to the fitting cylinder base end, and
wherein the base end of the needle hub is fitted into the fitting hole at a tip side of the fitting hole, and the chemical discharge tube of the outer cylinder is fitted into the fitting hole at a base end side of the fitting hole.

12. The chemical injection syringe according to claim 5, further comprising an elastic body disposed near the base end of the needle hub, the needle being inserted through the elastic body.

13. A method comprising:
injecting a chemical into a skin upper layer using the needle assembly according to claim 1.

* * * * *